United States Patent
Amano et al.

(10) Patent No.: US 7,566,309 B2
(45) Date of Patent: Jul. 28, 2009

(54) BLOOD WATER CONTENT DETECTION DEVICE AND HEMODIALYSIS TIMING DETERMINATION DEVICE

(75) Inventors: Kazuhiko Amano, Yokohama (JP); Hiroaki Tanaka, Fukuoka (JP)

(73) Assignee: Seiko Epson Corporation, Tokyo (JP)

( * ) Notice: Subject to any disclaimer, the term of this patent is extended or adjusted under 35 U.S.C. 154(b) by 1452 days.

(21) Appl. No.: 10/617,205

(22) Filed: Jul. 11, 2003

(65) Prior Publication Data

US 2004/0210144 A1    Oct. 21, 2004

(30) Foreign Application Priority Data

Jul. 12, 2002    (JP) .............................. 2002-203994

(51) Int. Cl.
*A61B 5/02* (2006.01)
*C02F 1/44* (2006.01)
*A61B 5/00* (2006.01)

(52) U.S. Cl. ................... 600/500; 600/310; 210/739

(58) Field of Classification Search .......... 600/310, 600/322, 481, 500, 502, 504; 210/739
See application file for complete search history.

(56) References Cited

U.S. PATENT DOCUMENTS 4,718,891 A * 1/1988 Lipps .......................... 604/31

6,459,930 B1    10/2002  Takehara et al.
6,740,044 B2 *  5/2004  Sato ............................ 600/485
6,808,627 B2 * 10/2004  Kawaguchi ................. 600/500

FOREIGN PATENT DOCUMENTS

| JP | A 2000-83914 | 3/2000 |
| JP | A-2001-000540 | 1/2001 |
| JP | A-2002-034946 | 2/2002 |
| JP | A 2002-52011 | 2/2002 |
| JP | A 2002-119488 | 4/2002 |

OTHER PUBLICATIONS

Amano, Kazuhiko, "Wearable Myakuha Monitor ni yoru Ketsueki Tosekichu no Junkan Dotai Sokutei no Kokoromi" (in Japanese), Micromechatronics (Journal of the Horological Institute of Japan), Mar. 10, 2003, vol. 47, No. 1, pp. 72-80.*

* cited by examiner

*Primary Examiner*—Eric F Winakur
(74) *Attorney, Agent, or Firm*—Oliff & Berridge, PLC

(57) ABSTRACT

A blood water content detection device includes a pulse wave detection section which noninvasively detects a peripheral pulse wave, and an index extraction section which extracts an index which changes depending on a blood water content from the detected pulse wave. The blood water content detection device may include a low-cut section which removes a low frequency component which becomes noise from the pulse wave detected by the pulse wave detection section. The blood water content detection device may further include first and second differentiation sections. The index extraction section extracts a pulse height ratio (b/a) or (d/a) of a second differential waveform as the index, for example.

26 Claims, 19 Drawing Sheets

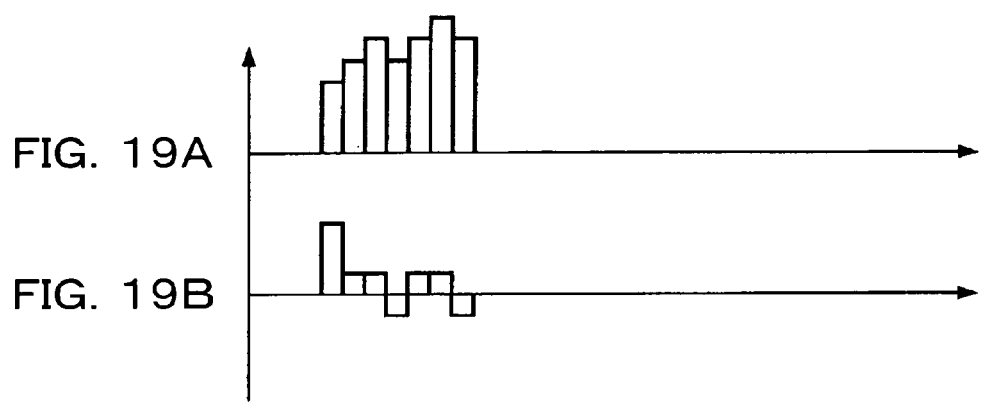
FIG. 19A
FIG. 19B
FIG. 20
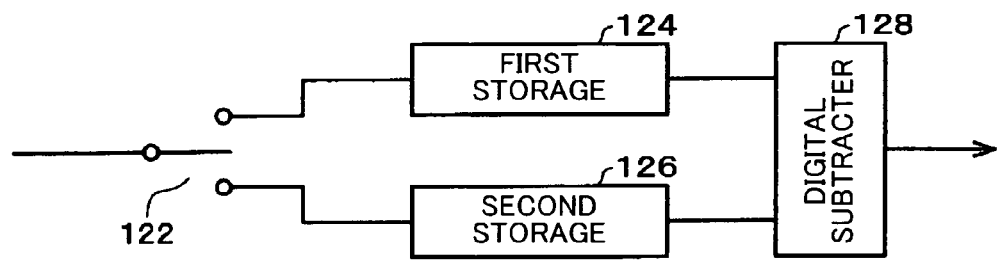

BLOOD WATER CONTENT DETECTION DEVICE AND HEMODIALYSIS TIMING DETERMINATION DEVICE

Japanese Patent Application No. 2002-203994 filed on Jul. 12, 2002, is hereby incorporated by reference in its entirety.

BACKGROUND OF THE INVENTION

The present invention relates to a device which detects the blood water content of a subject, and a hemodialysis timing determination device using the same.

Since a chronic dialysis patient cannot remove wastes and water, the patient must pay attention to daily life including intake of water and meals. Hemodialysis for a chronic dialysis patient is generally performed three times a week, in which three to four liters of water are removed for four to five hours.

Since the patient cannot know the state inside the body after hemodialysis, the patient cannot but maintain precautions in daily life. Therefore, the daily life of the patient is restricted to a large extent.

The patient must go to the hospital at a predetermined time and undergo periodic hemodialysis. However, the time at which the patient should undergo hemodialysis should vary depending on a change in immunity of the patient and the like.

BRIEF SUMMARY OF THE INVENTION

The present invention may provide a blood water content detection device which enables a change in state inside the body to be recognized after hemodialysis by detecting the blood water content of the chronic dialysis patient.

The present invention may also provide a hemodialysis timing determination device capable of determining the time when hemodialysis is necessary or the time when hemodialysis is completed, based on the detected blood water content.

According to one aspect of the present invention, there is provided a blood water content detection device comprising: a pulse wave detection section which noninvasively detects a peripheral pulse wave; and an index extraction section which extracts an index which changes depending on a blood water content from the detected pulse wave.

The pulse wave detection section noninvasively detects the peripheral pulse wave by optically detecting the pulse wave of a subject or detecting the pulse wave from the pulse pressure. Since the index extracted by the index extraction section changes depending on the blood water content, the blood water content can be recognized from the index.

As the index which changes depending on the blood water content, a pulse height of a dicrotic notch in the pulse wave can be given. The pulse height of the dicrotic notch in the pulse wave has a correlation with extensibility of blood vessels in early-systole. Since extension of blood vessels is mainly caused by an increase in blood water content in the case of a chronic dialysis patient, the pulse height of the dicrotic notch in the pulse wave is suitable as the index which changes depending on the blood water content.

Since the absolute value of the pulse height of a second differential waveform is unstable, a stable relative value may be used as the index. As the relative value used as the index, a ratio (or a first ratio) of a pulse height of a first rise point of one cycle of the pulse wave and a pulse height of the dicrotic notch can be given.

As another index which changes depending on the blood water content, a pulse height of an ejection wave in the pulse wave can be given. The pulse height of the ejection wave in the pulse wave also has a correlation with extensibility of blood vessels in early-systole in the same manner as the pulse height of the dicrotic notch in the pulse wave. As a relative index corresponding to the pulse height of the ejection wave, a ratio (or a first ratio) of a pulse height of the first rise point of one cycle of the pulse wave and a pulse height of the ejection wave can be given.

The index extraction section may further extracts a reference index which is less dependent on the blood water content than the above first ratio, and may output a ratio of the index (or the first ratio) to the reference index. As the reference index, a ratio (or a second ratio) of the pulse height of the first rise point of one cycle of the pulse wave and a pulse height of a dicrotic wave can be given. In this case, the index extraction section outputs (the first ratio)/(the second ratio) as the index.

The blood water content detection device may further comprise a low-cut section which removes a low frequency component due to changes caused by activities of an autonomic nervous system (excluding movement of blood vessels) from the pulse wave detected by the pulse wave detection section.

The low frequency component is not a frequency component of a pulse wave which occurs when blood flows from aorta to peripheral vessels based on expansion and contraction of the heart, and is a frequency component lower than the frequency component of such pulse wave. The low frequency component becomes noise which is superimposed on the pulse wave. The pulse wave can be detected with high accuracy by eliminating the noise.

The low-cut section may further remove a low frequency component caused by body movement of a subject in a resting state. Even if the subject is in a resting state, there is body movement to maintain the resting state or because of other reasons. The body movement is not conscious quick movement of the limbs, but relatively slow movement. Therefore, since the low frequency component due to body movement is superimposed on the pulse wave and becomes noise, this low frequency component is also removed.

The low-cut section may set the low-cut frequency range from 0.4 to 0.5 Hz. Noise can be effectively eliminated without impairing the features of the pulse waveform by removing the low frequency component by setting the low-cut frequency range from 0.4 to 0.5 Hz. The low frequency component due to changes caused by activities of an autonomic nervous system (excluding movement of blood vessels) and the low frequency component caused by the body movement of a subject in the resting state are lower than the low-cut frequency from 0.4 to 0.5 Hz. Moreover, the characteristics of the pulse wave are not included in the frequency component lower than the low-cut frequency.

The low-cut section may remove a low frequency component (about 0.1 Hz, for example) due to changes caused by the activities of the sympathetic nervous system such as a change in the muscle pump which occurs about every 10 seconds.

The low-cut section may further remove a low frequency component (about 0.15 Hz, for example) due to changes caused by activities of the parasympathetic nervous system such as respiratory activities.

The low-cut section may be formed of a bandpass filter which sets the high-cut frequency range from 16 to 30 Hz. This enables a useless high frequency component exceeding the high-cut frequency to be removed. It suffices that the high-cut frequency be set at 30 Hz. The high-cut frequency may be set at 20 Hz or 16 Hz.

The blood water content detection device may further comprise a first differentiation section which differentiates the pulse wave from which the low frequency component has been removed; and a second differentiation section which differentiates the pulse wave differentiated by the first differentiation section. The characteristics of the pulse wave are further exposed in a pulse waveform obtained by double differentiation of the pulse wave from which the low frequency component has been removed.

The low-cut section and the first differentiation section may be formed by an analog differentiation circuit. The analog differentiation circuit may differentiate the pulse wave which is an analog signal output from the pulse wave detection section, and have high-pass characteristics. Alternatively, the analog differentiation circuit may differentiate the pulse wave which is an analog signal output from the pulse wave detection section, and have bandpass characteristics.

The blood water content detection device may further include a quantization section which quantizes output from the pulse wave detection section. In this case, the low-cut section may include a Fourier transformation section which performs Fourier transformation of quantized data, a digital filter which removes a frequency spectrum lower than the low-cut frequency, and an inverse Fourier transformation section which performs inverse Fourier transformation of output from the digital filter. In this case, at least one of the first differentiation section and the second differentiation section may be formed by a quantization differentiation section which calculates inclination of two different points on a time base.

The quantization section may be formed of an analog-digital converter which performs automatic gain control in which the pulse wave is amplified so that amplitude of the pulse wave is equal to or greater than a predetermined amplitude level within a dynamic range.

A second differential waveform which is output from the second differentiation section may have five inflection points having pulse heights "a" to "e" on a time base in that order within one cycle; and the index extraction section may extracts the index based on at least one of the five pulse heights.

The pulse heights "a" to "e" have no unit. The pulse heights "a" to "e" output from an amplifier are subjected to automatic gain control and output so that the maximum amplitude is obtained within the dynamic range.

The pulse height "a" corresponds to the first rise point of one cycle of a pulse wave, and the pulse height "b" corresponds to a point immediately before the first half peak point of the ejection wave. The pulse height "c" corresponds to a rise point of the tidal wave, and the pulse height "d" corresponds to the degree of inclination of a point between the peak point of the tidal wave (in late-systole) and the dicrotic notch. The pulse height "e" corresponds to the degree of inclination of a point between the dicrotic notch and the dicrotic wave.

In more detail, the pulse height "a" is a peak which indicates an increase in acceleration of the pre-systolic pressure accompanying contraction of the heart at the start of systole. The pulse height "b" is a peak which indicates a decrease in the maximum acceleration in early-systole which occurs accompanying an increase in ejection rate in systole. This pulse height "b" means the degree of opening of aorta, and indicates extensibility of blood vessels in early-systole. The pulse height "c" is a peak which indicates an increase in acceleration which occurs from early-systole to late-systole. The pulse height "d" indicates a change in acceleration in late-systole due to superimposition of a reflected pressure wave from the peripheral on the driving (ejection) pressure wave in early-systole. This pulse height "d" shows extensibility of blood vessels in late-systole. The pulse height "e" is a peak which indicates a change in acceleration at a notch which occurs due to closing of aortic valve in response to superimposition of the reflected pressure wave in late-systole.

The pulse height "d" or the pulse height "b" of the second differential waveform may be extracted as the above index. In the case where the first ratio is used as the index, the pulse height ratio (d/a) or the pulse height ratio (b/a) may be extracted. In the case where (the first ratio)/(the second ratio) is used as the index, the pulse height ratio [(d/a)/(e/a)], the pulse height ratio [(b/a)/(c/a)], or the like may be extracted. The pulse height ratio [(d/a)/(b/a)] may also be used.

As another index which changes depending on the blood water content, a cardiac ejection time, a cardiac diastolic time, a ratio of a cardiac ejection time to one cycle of the pulse wave, or a ratio of a cardiac diastolic time to one cycle of the pulse wave can be given. These indices can be detected from the second differential waveform. However, these indices can be detected without using the second differential waveform as described later.

According to another aspect of the present invention, there is provided a hemodialysis timing determination device comprising: the above blood water content detection device; and a determination section which determines the timing of hemodialysis based on the output of the blood water content detection device.

The index output from the blood water content detection device has a correlation with the water increase rate or the water removal rate in blood of a chronic dialysis patient. Therefore, the determination section may compare the index output from the blood water content detection device with a comparative value corresponding to the time when hemodialysis is necessary (or a blood water content upper limit, or water increase upper limit), and determine the time when hemodialysis is necessary based on the comparison result. The determination section may compare the index output from the blood water content detection device with a comparative value corresponding to the time when hemodialysis is completed (or a blood water content lower limit, or water removal lower limit), and determine the time when hemodialysis is completed based on the comparison result.

BRIEF DESCRIPTION OF THE SEVERAL VIEWS OF THE DRAWING

FIG. 19 is a waveform chart showing a quantization waveform and a differential waveform of the quantization waveform.

FIG. 20 is a block diagram showing a configuration example of a second differentiation section shown in FIG. 17.

DETAILED DESCRIPTION OF THE EMBODIMENT

The hemodialysis timing determination device having the blood water content detection device according to one embodiment of the present invention is described below with reference to the drawings.

External Configuration of Hemodialysis Timing Determination Device

Figure 1A:
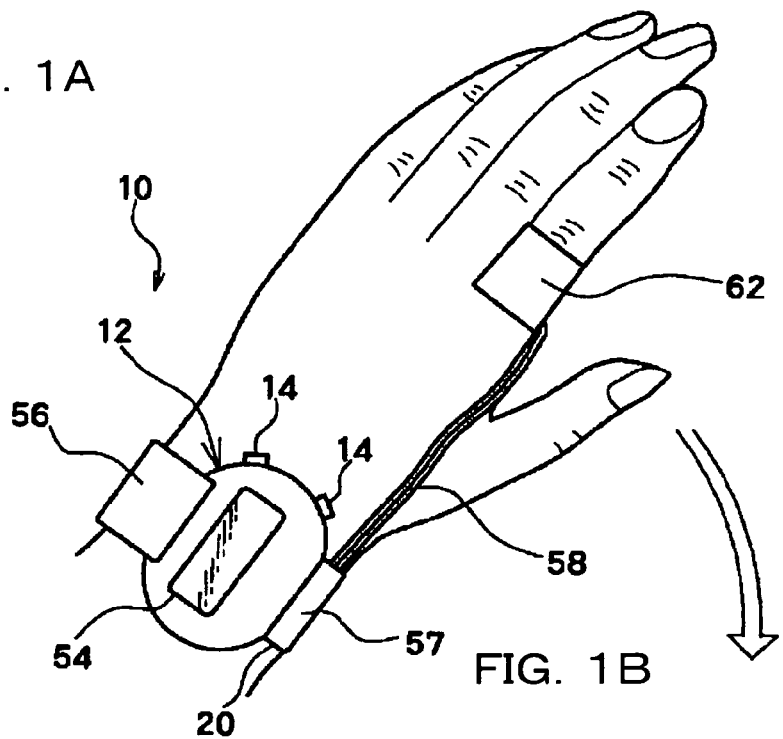
FIGS. 1A to 1C are external views showing a blood water content detection device according to the embodiment of the present invention.
Figure 1B:
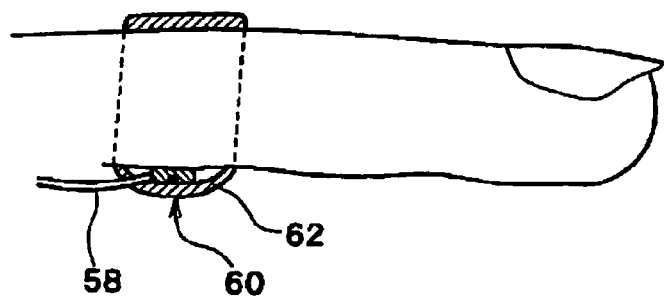
Figure 1C:
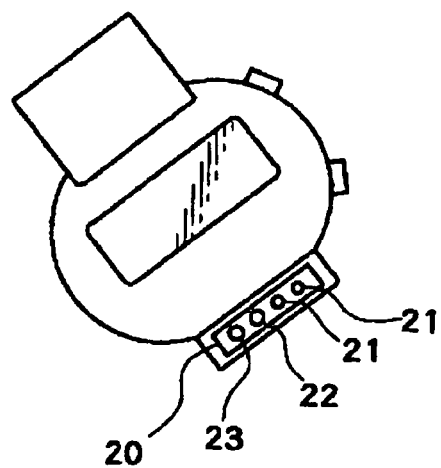

The hemodialysis timing determination device according to this embodiment is a portable type device which is attached to the wrist of a subject, for example. The hemodialysis timing determination device may have an external configuration as shown in FIGS. 1A, 1B, and 1C. A hemodialysis timing determination device 10 includes a body 12 having a structure in the shape of a wristwatch, a cable 58 which is connected to a connector section 20 of the body 12 through a connector piece 57, and a pulse wave detection section 60 provided to the end of the cable 58. A wrist band 56 is attached to the body 12, and the body 12 is installed on the wrist of a subject by using the wrist band 56.

The body 12 includes the connector section 20. The connector piece 57, which is the end of the cable 58, is removably attached to the connector section 20.

FIG. 1C shows the connector section 20 from which the connector piece 57 is removed. The connector section 20 includes connection pins 21 which are connected with the cable 58, an LED 22 and a phototransistor 23 for transferring data, and the like.

A display section 54 consisting of a liquid crystal panel is formed on the surface side of the body 12. The display section 54 has a segment display region, a dot display region, and the like. The display section 54 displays an index in the pulse wave which changes depending on the blood water content, the time of hemodialysis determined based on the index, and the like. A display device other than a liquid crystal panel may be used as the display section 54.

The body 12 includes a central processing unit (CPU) which controls various calculations and conversions, and a memory which stores a program for operating the CPU and the like (not shown). Button switches 14 for performing various operations and input are provided on the periphery of the body 12.

As shown in FIG. 1B, the pulse wave detection section 60 is installed near the root of the forefinger of a subject while being shaded by a sensor securing band 62. Since the length of the cable 58 is decreased by installing the pulse wave detection section 60 near the root of the finger, the subject is not disturbed if the pulse wave detection section 60 is installed. Moreover, since the change in blood flow due to temperature is small near the root of the finger in comparison with the fingertip, the pulse waveform to be detected is comparatively less influenced by temperature or the like.

Pulse Wave Detection Section

Figure 2:
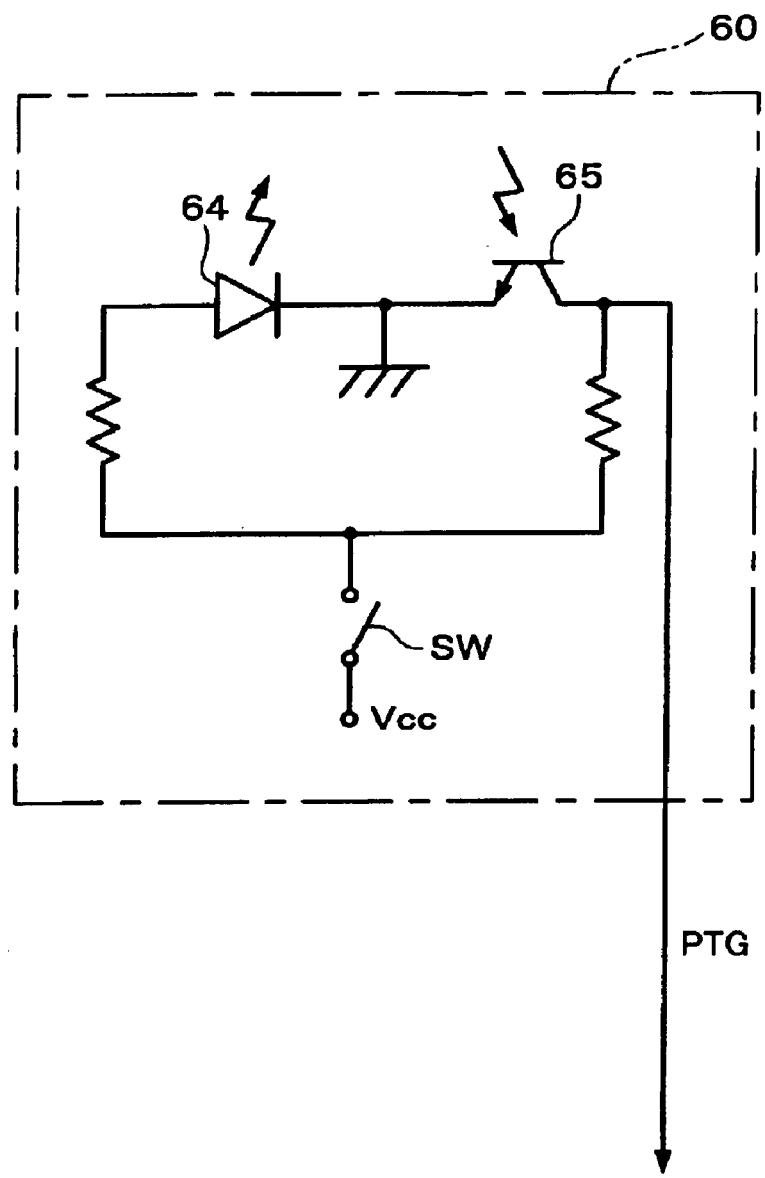
FIG. 2 is a circuit diagram showing an example of the circuit configuration of a pulse wave detection section in FIG. 1A.

As shown in FIG. 2, the pulse wave detection section 60 includes an LED 64, a phototransistor 65, and the like so that the peripheral pulse wave can be detected noninvasively, specifically, without breaking the skin. The pulse wave detection section 60 utilizes a phenomenon in which the pulse waveform is almost the same as the waveform of a change in blood flow (plethysmogram waveform), and detects the pulse wave (plethysmogram) by using a photosensor formed to emit light to a capillary plexus and to detect a change in the amount of light reflected by or transmitted through the blood in the capillary blood vessel.

In more detail, when a power supply voltage is applied to the pulse wave detection section 60 by turning on a switch SW, light is emitted from the LED 64. The emitted light is reflected by the blood vessel or tissue of the subject and received by the phototransistor 65. Therefore, a photocurrent of the phototransistor 65 is converted into a voltage and output as a signal PTG of the pulse wave detection section 60.

The emission wavelength of the LED 64 is selected near the peak of the absorption wavelength of hemoglobin in blood. Therefore, the light receiving level changes depending on the blood flow. Therefore, the pulse waveform is detected by detecting the light receiving level. As the LED 64, an InGaN (indium-gallium-nitrogen) based blue LED is suitably used. The emission spectrum of the LED may have an emission peak at about 450 nm and an emission wavelength region ranging from 350 to 600 nm.

In this embodiment, a GaAsP (gallium-arsenic-phosphorus) based phototransistor may be used as the phototransistor 65 corresponding to the LED having the above emission characteristics. The phototransistor 65 may have a main sensitivity region at 300-600 nm and also have a sensitivity region at 300 nm or less.

The pulse wave can be detected in a wavelength region of 300-600 nm by combining the blue LED 64 with the phototransistor 65. This contributes to the following advantages.

Since light having a wavelength region of 700 nm or less contained in external light is rarely transmitted through the tissue of the finger, the light having a wavelength region of 700 nm or less does not reach the phototransistor 65 through the tissue of the finger even if external light is applied to the finger in the area in which the finger is not covered with the sensor securing band. Only light having a wavelength region which does not influence detection of the pulse wave reaches the phototransistor 65. Light having a wavelength region smaller than 300 nm is almost completely absorbed on the surface of the skin. Therefore, the substantial light receiving wavelength region is 300 to 700 nm even if the light receiving wavelength region is set to 700 nm or less. Therefore, the influence of external light can be prevented without entirely covering the finger. Hemoglobin in blood has a large absorption coefficient for light having a wavelength of 300 to 700 nm, which is several to about one hundred times or more greater than the absorption coefficient for light having a wavelength of 880 nm. Therefore, if light having a wavelength region for which the absorption coefficient of hemoglobin is great (300 to 700 nm) is used as the detection light as in this example, the detected value changes with high sensitivity corresponding to the change in blood flow. Therefore, the SN ratio of the pulse waveform based on the change in blood flow can be increased.

The pulse wave detection section 60 takes the pulse wave which changes corresponding to the blood flow (plethysmogram) as the change in the amount of erythrocytes in the capillary plexus present near the skin, and detects the pulse wave as the change in the amount of transmission or reflection of light applied to the skin. Therefore, the pulse wave can be detected without placing the sensor at the position of the peripheral artery such as the radial artery or digital artery. Therefore, the pulse wave detection section 60 is capable of stably detecting the change in the amount of erythrocytes in the capillary blood vessel present near the skin as the pulse wave (plethysmogram) in the peripheral artery. In addition, light having a near-infrared wavelength region (880 nm or more) which has good transmissivity to the subcutaneous tissue and for which hemoglobin has absorption characteristics may be employed.

The pulse wave detection section 60 may detect the pulse wave based on the pulse pressure. The pulse wave detection section 60 may be attached to a part other than the root of the finger as described later. For example, the pulse wave detection section 60 may detect the pulse wave from the earlobe.

Basic Functional Block Configuration and Low-cut Section

Figure 3:
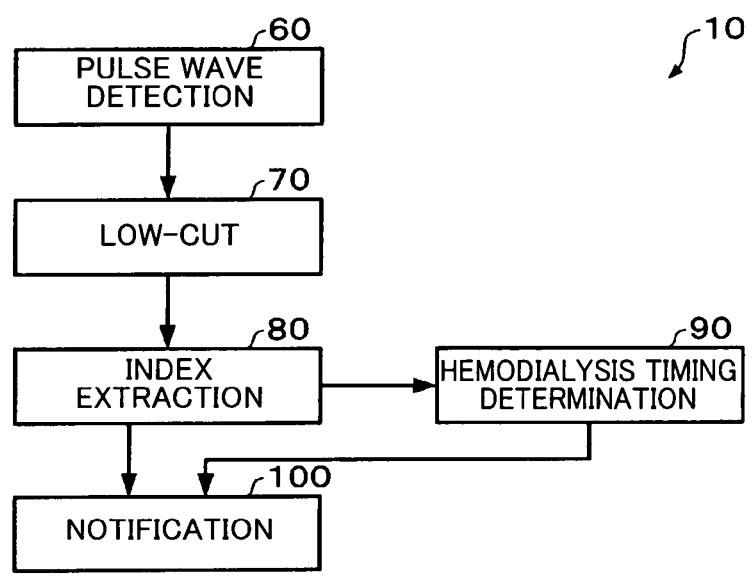
FIG. 3 is a block diagram showing basic functions of the embodiment of the present invention.

FIG. 3 is a functional block diagram showing the hemodialysis timing determination device 10 according to this embodiment. The hemodialysis timing determination device 10 shown in FIG. 3 includes a low-cut section 70, an index extraction section 80, a hemodialysis timing determination section 90, and a notification section 100 in addition to the pulse wave detection section 60. The low-cut section 80 is not necessarily an indispensable component. The time of hemodialysis is preferably determined after resting or at least in a resting state for a subject to whom the hemodialysis timing determination device 10 is attached. However, a low frequency component due to changes caused by activities of the autonomous nervous system (excluding movement of blood vessels) of the subject, or a low frequency component caused by movement of the body of the subject (body movement) in a resting state is superimposed on the pulse wave to be detected even after resting or in a resting state. Such a low frequency component becomes noise when detecting the blood water content. Detection accuracy can be increased by eliminating the noise by using the low-cut section 70. The details of the low-cut section 70 are described later.

Pulse Waveform and Index Extraction Section

Figure 4:
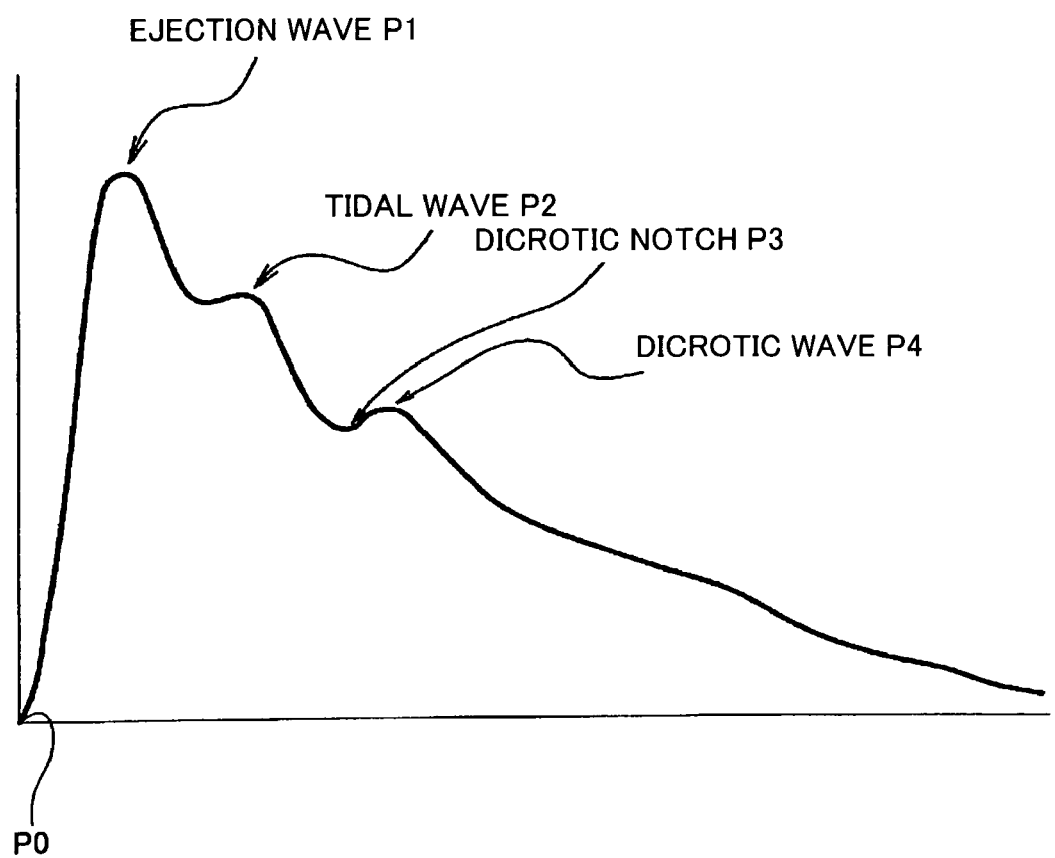
FIG. 4 is a waveform chart showing one cycle of a pulse wave detected by the pulse wave detection section.

FIG. 4 is a characteristic diagram showing a typical pulse waveform in an artery such as the radial artery. The pulse wave in one cycle shown in FIG. 4 has peaks including a first rise point P0 of one cycle of the pulse wave, an ejection wave P1, a tidal wave P2, a dicrotic notch P3, and a dicrotic wave P4.

According to an experiment conducted by the present inventor, it was confirmed that the ejection wave P1 or the dicrotic notch P3 among the above features of the pulse wave changes depending on extensibility of blood vessels, and therefore is an index which changes depending on the blood water content. The extensibility of blood vessels is dependent on the volume of blood, and the volume of blood is increased as the blood water content is increased. Since the blood water content of a hemodialysis patient is increased after hemodialysis, the time at which the blood water content exceeds a predetermined value can be determined as the time when hemodialysis is necessary based on the ejection wave P1 or the dicrotic notch P3 as the index.

The index extraction section 80 shown in FIG. 3 extracts the index based on the ejection wave P1 or the dicrotic notch P3. The hemodialysis timing determination section 90 shown in FIG. 3 determines the time of hemodialysis based on the index extracted by the index extraction section 80.

Figure 5:
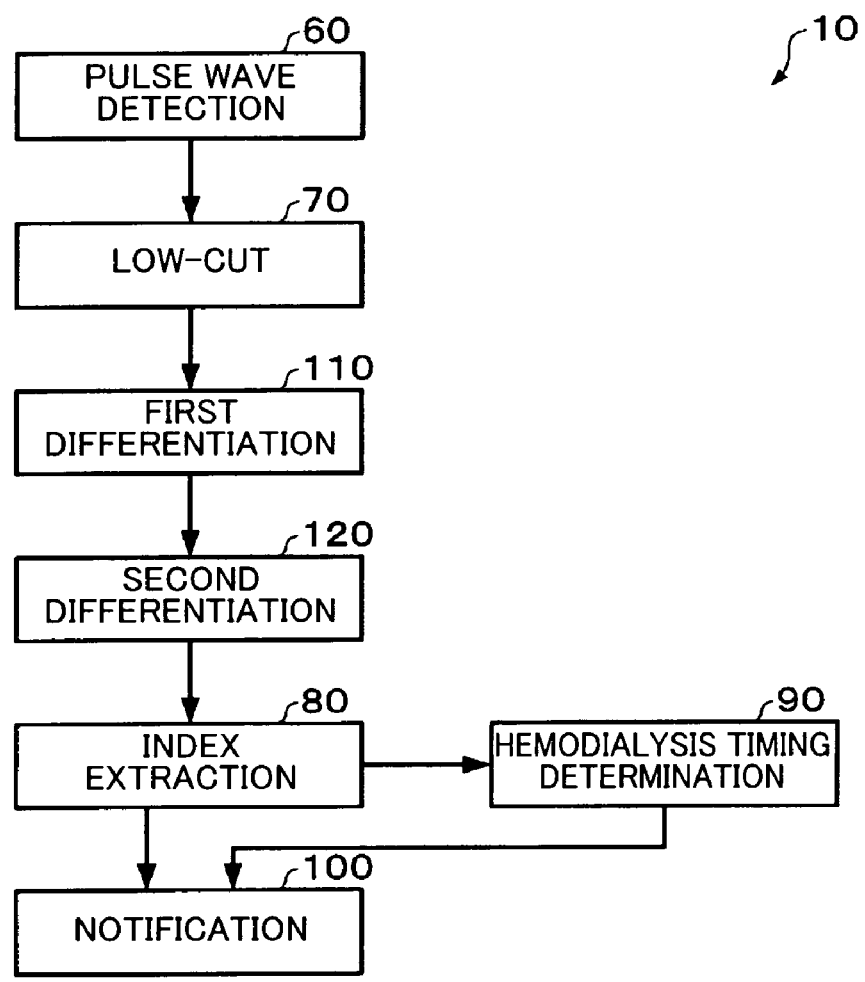
FIG. 5 is a functional block diagram in which first and second differentiation sections are added to the block diagram of basic functions of FIG. 3.

The index extraction section 80 may extract the index from the pulse wave shown in FIG. 4. However, the index extraction section 80 may extract the index based on a second differential waveform of the pulse wave. The features of the pulse wave shown in FIG. 4 become more significant in the second differential waveform. As shown in FIG. 5, a first differentiation section 110 and a second differentiation section 120 may be further provided in addition to the basic functional block configuration shown in FIG. 3.

Figure 6:
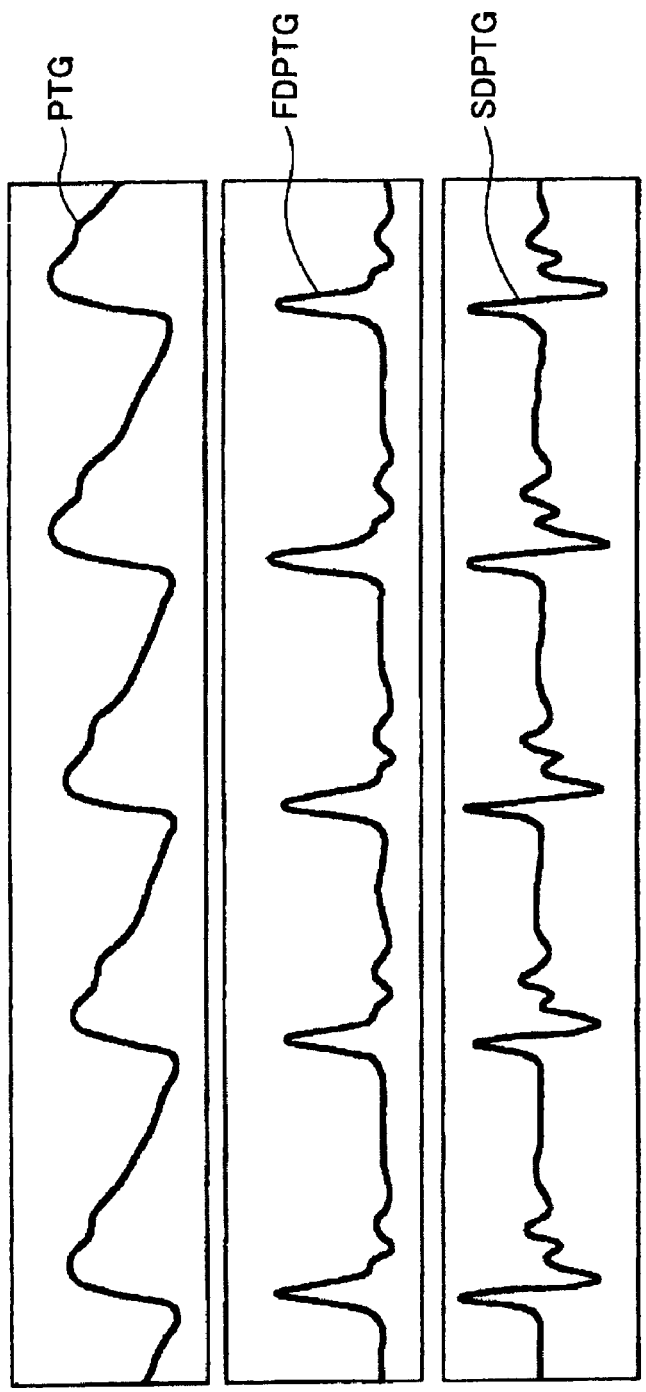
FIG. 6A is a waveform chart showing an original waveform of a detected pulse wave.
FIG. 6B is a waveform chart showing a first differential waveform of the original waveform of FIG. 6A.
FIG. 6C is a waveform chart showing a second differential waveform of the original waveform of FIG. 6A.
Figure 7:
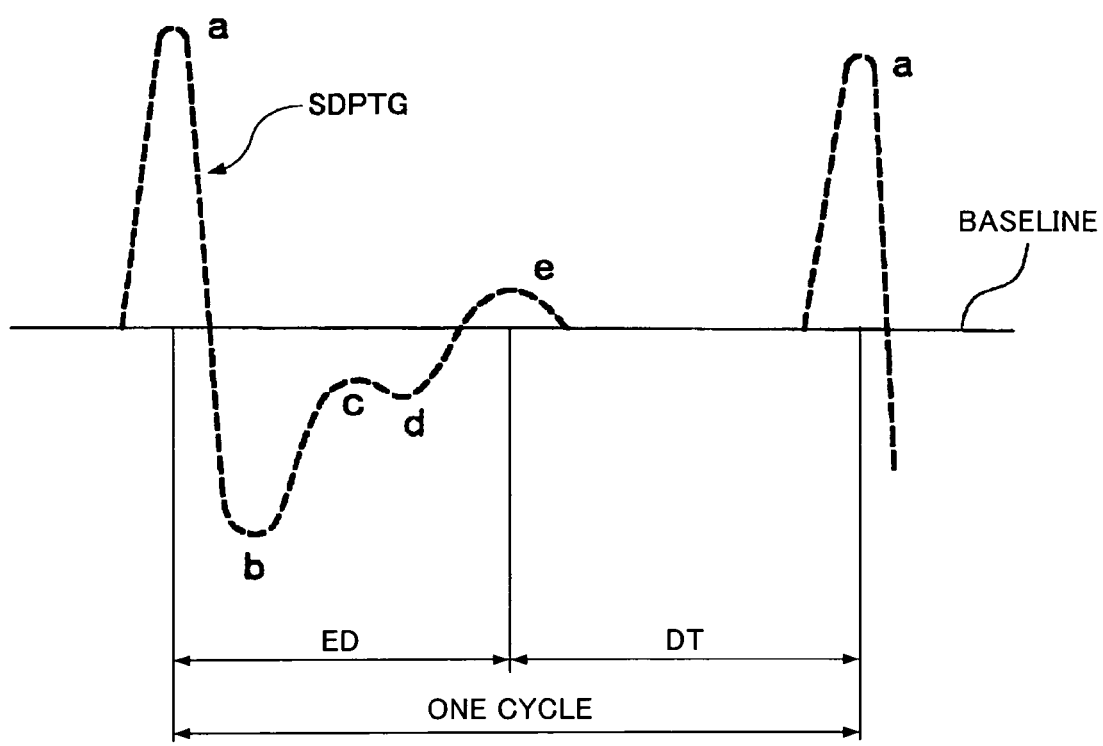
FIG. 7 is a schematic diagram for illustrating characteristics of a second differential waveform.

FIG. 6A is a waveform chart showing an original waveform PTG of the pulse wave detected by the pulse wave detection section 60 (or the pulse wave from which a low frequency component is removed by the low-cut section 70). FIG. 6B is a waveform chart showing a first differential waveform FDPTG (velocity waveform) obtained by differentiating the original waveform PTG by the first differentiation section 110. FIG. 6C is a waveform chart showing a second differential waveform SDPTG (acceleration waveform) obtained by differentiating the first differential waveform FDPTG by the second differentiation section 120. As shown in FIG. 7, the second differential waveform SDPTG has five more definite inflection points than the original waveform PTG The pulse heights of the five inflection points are referred to as a to e.

The pulse height "a" corresponds to the first rise point P0 of one cycle of the pulse wave. The pulse height "b" corresponds to a point immediately before the peak point of the ejection wave P1. The pulse height "c" corresponds to the rise point of the tidal wave P2. The pulse height "d" corresponds to the degree of inclination from the peak point of the tidal wave P2 (late-systole) to the dicrotic notch P3. The pulse height "e" corresponds to the degree of inclination from the dicrotic notch P3 to the dicrotic wave P4. Since the ejection wave P1 or the dicrotic notch P3 is the index which changes depending on the blood water content, the index extraction section 80 may extract the pulse height "b" or the pulse height "d" as the index.

The pulse height "b" or the pulse height "d" may be extracted as an absolute value. However, the absolute value may differ depending on a change in physical condition, a change in amplification factor, influence of noise, and the like, even if the blood water content is the same.

Therefore, the index extraction section 80 preferably calculates the ratio of the pulse height "b" or the pulse height "d" to the pulse height which can become a reference value of the pulse height of the pulse wave, such as the pulse height "a". Specifically, the index extraction section 80 calculates the ratio b/a or the ratio d/a.

In the case where the ratio b/a or the ratio d/a is defined as a first ratio, the index extraction section 80 may further extract a reference index which is less dependent on the blood water content than the first ratio. As the reference index, a ratio (second ratio) of the pulse height "e" which corresponds to the degree of inclination from the dicrotic notch P3 to the dicrotic wave P4 to the pulse height "a" which corresponds to the first rise point P0 of one cycle of the pulse wave can be given. In this case, the index extraction section 80 calculates the ratio of the index (first ratio) to the reference index (second ratio), specifically, the pulse height ratio [(d/a)/(e/a)] or the pulse height ratio [(b/a)/(e/a)]. The index extraction section 80 may calculate the pulse height ratio [(d/a)/(b/a)]. This enables the blood water content to be detected with higher accuracy.

Correlation Between Index b/a or d/a and Blood Water Content

Figure 8:
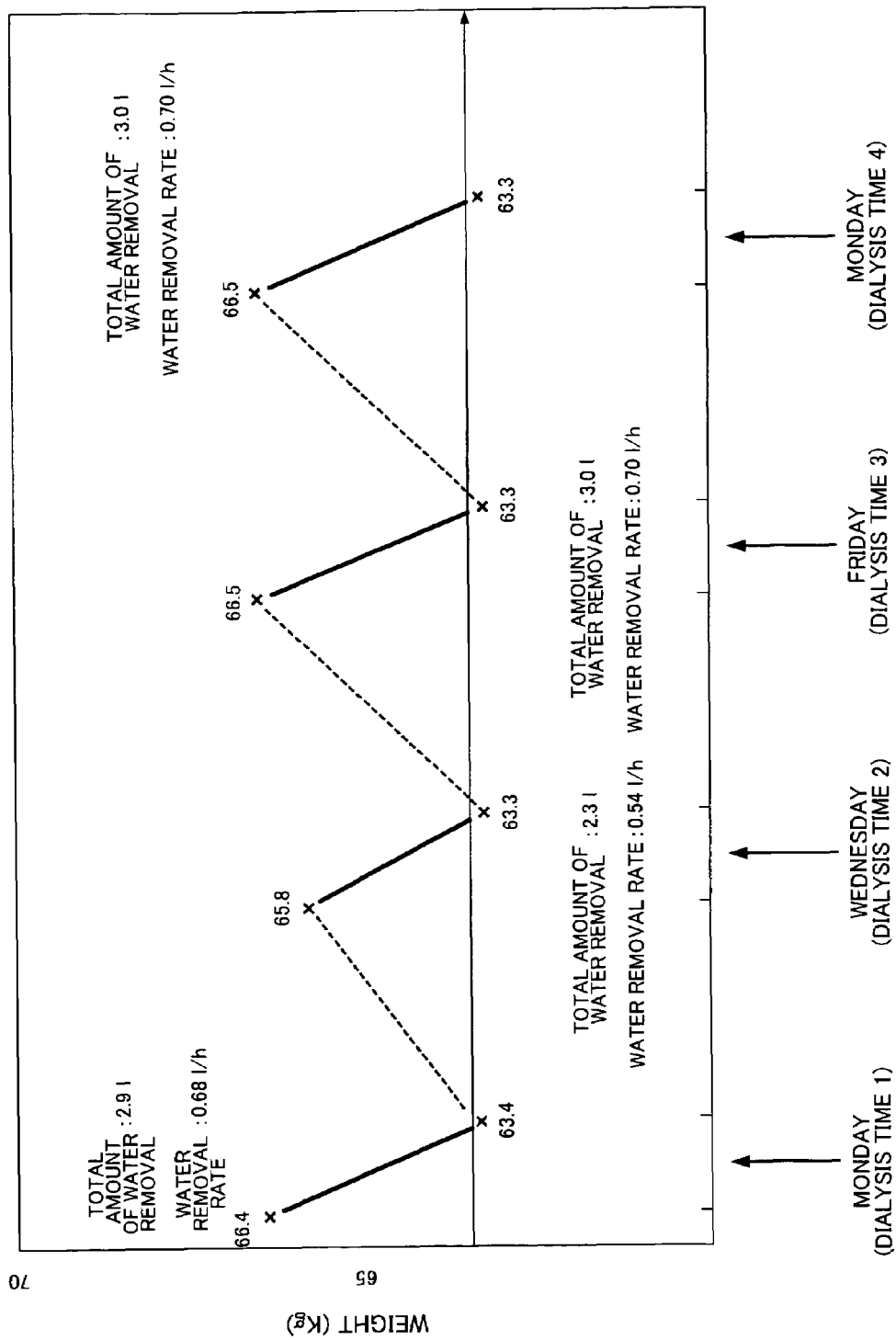
FIG. 8 is a schematic diagram for illustrating measurement time of the experiments carried out during hemodialysis.

The present inventor attached the device of the present invention to a chronic glomerulonephritis patient, and measured the index b/a and the index d/a. As shown in FIG. 8, the measurement was conducted during dialysis carried out on Monday (time 1), Wednesday (time 2), Friday (time 3), and the next Monday (time 4). A solid line shown in FIG. 8 indicates a dialysis period, in which the weight of the patient is decreased due to a decrease in blood water content. A dotted line shown in FIG. 8 indicates a non-dialysis period, in which the weight of the patient is increased due to an increase in blood water content.

Figure 9:
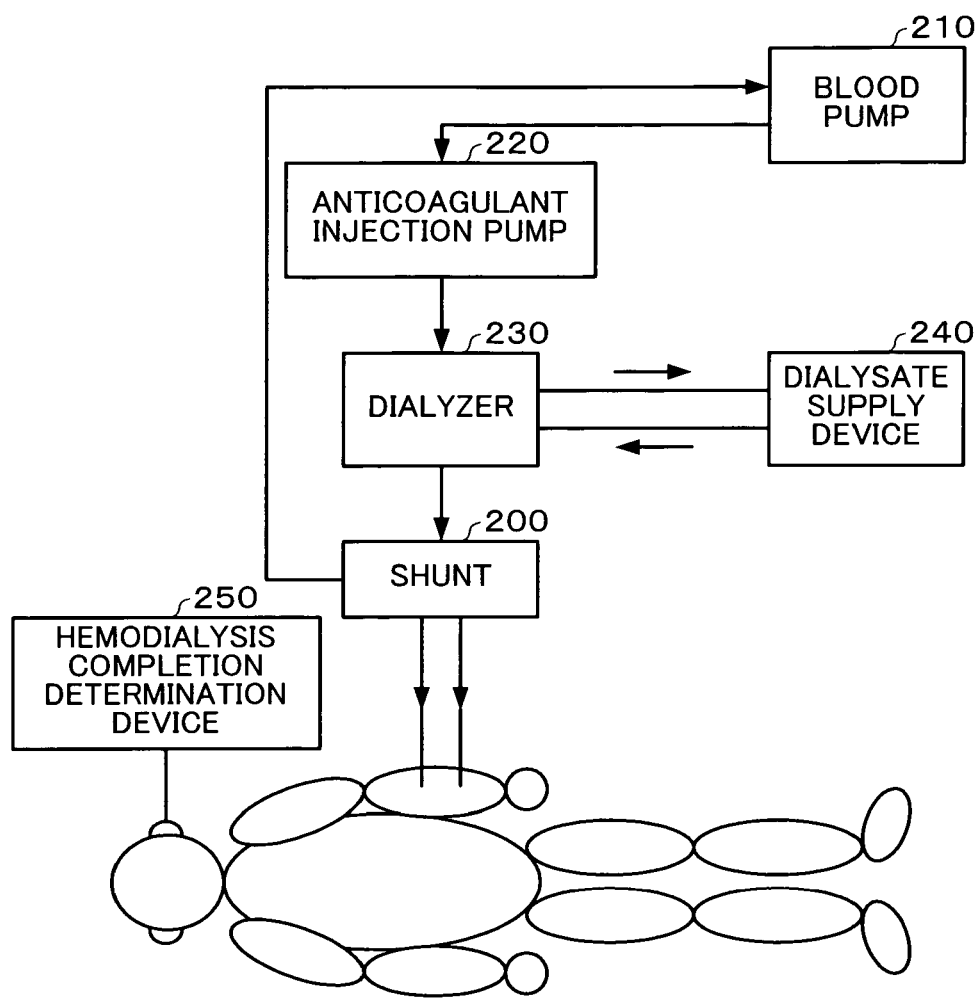
FIG. 9 is a block diagram showing a dialyzer and a hemodialysis completion determination device.

As shown in FIG. 9, hemodialysis is carried out by connecting the blood vessel of the patient to a dialyzer 230 through a shunt 200, a blood pump 210, and an anticoagulant injection pump 220. A dialysate is supplied to the dialyzer 230 from a dialysate supply device 240. In the dialyzer 230, unnecessary substances in the blood are transferred to the dialysate and useful substances are transferred to the blood. The blood after dialysis is returned to the body.

In FIG. 9, a hemodialysis completion determination device 250 used during dialysis is a stationary type device which is attached to the earlobe of the patient, for example, and determines the hemodialysis completion based on the pulse wave in the earlobe, differing from the portable type device shown in FIGS. 1A to 1C. Dialysis is ended when the hemodialysis completion determination device 250 notifies the patient of the hemodialysis completion. Therefore, it is unnecessary to determine the water removal amount for each patient and to end dialysis by monitoring the water removal amount. The operations of the pumps 210 and 220 and the dialysate supply device 240 may be automatically ended based on a completion notification signal from the hemodialysis completion determination device 250. The time when hemodialysis is necessary may be determined by the device shown in FIG. 1A in the non-dialysis period by allowing the patient to carry the device. The time when hemodialysis is necessary may be determined in a period other than hemodialysis by attaching the device shown in FIG. 9 to the earlobe or fingertip of the patient.

Figure 10:
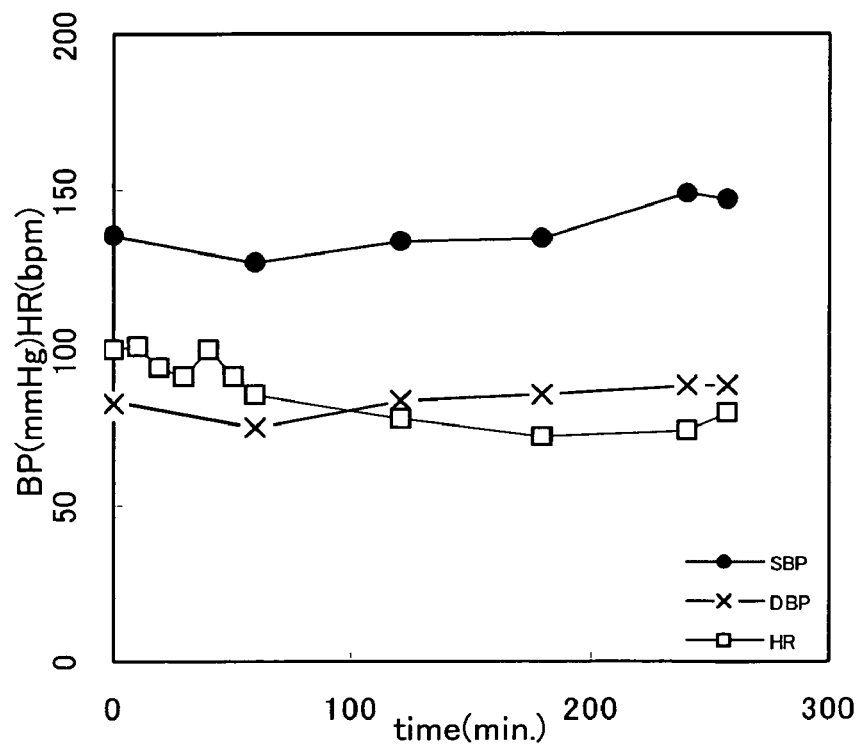
FIG. 10 is a measurement diagram of a blood pressure (systolic blood pressure SBP and diastolic blood pressure DBP) and a heart rate HR measured at the dialysis time 3 in FIG. 8.
Figure 11:
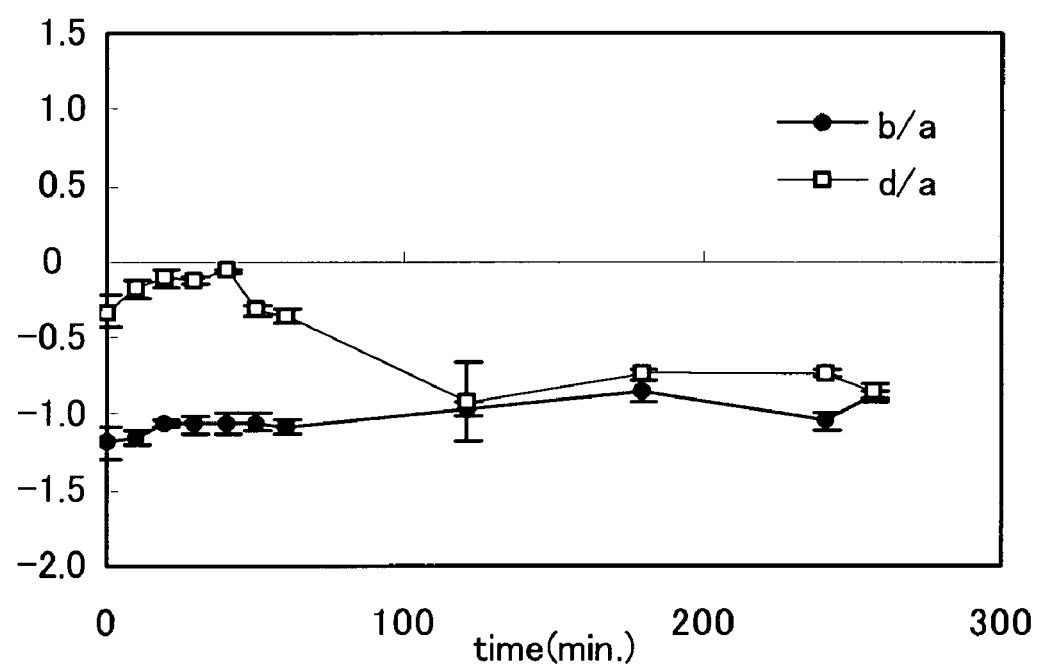
FIG. 11 is a measurement diagram of indices b/a and d/a measured at the dialysis time 3 in FIG. 8.

FIG. 10 shows measurement results for changes in blood pressure and pulse rate during the third dialysis for the chronic renal failure patient shown in FIG. 8, in which the device is attached to the root of the finger. FIG. 11 shows b/a and d/a. The horizontal axis in each figure indicates the time elapsed during dialysis. Since water in blood is removed by hemodialysis, the horizontal axis in each figure is equivalent to the water removal amount. In FIG. 10, HR indicates the heart rate, DBP indicates the diastolic blood pressure (minimum blood pressure), and SBP indicates the systolic blood pressure (maximum blood pressure).

As is clear from FIG. 11, the index b/a had a positive correlation with the dialysis time (water removal amount). Since the blood water content is decreased as the dialysis time elapses, the cardiac contractile force is increased. Therefore, the heart pumps blood into the aorta, whereby extensibility of the blood vessels is decreased. This change appears in the index b/a, whereby the index b/a is increased as the dialysis time elapses.

As is clear from FIG. 11, the index d/a had a negative correlation with the dialysis time (water removal amount). An artery is dominated by the autonomic nerves in small and medium blood vessels. However, the sympathetic nerve becomes predominant as the dialysis time elapses, whereby the blood vessels contract. This change appears in the index d/a, whereby the index d/a is decreased as the dialysis time elapses.

Therefore, if the device of the present invention is attached to the patient during hemodialysis and the index is monitored during the hemodialysis, the time when hemodialysis is completed can be determined. In more detail, the hemodialysis timing determination section 90 shown in FIG. 5 stores a water removal lower limit (blood water content lower limit) corresponding to the dialysis completion as a comparative value. The determination section 90 determines the time when hemodialysis is completed by comparing the index output from the index extraction section 80 with the comparative value.

Figure 12:
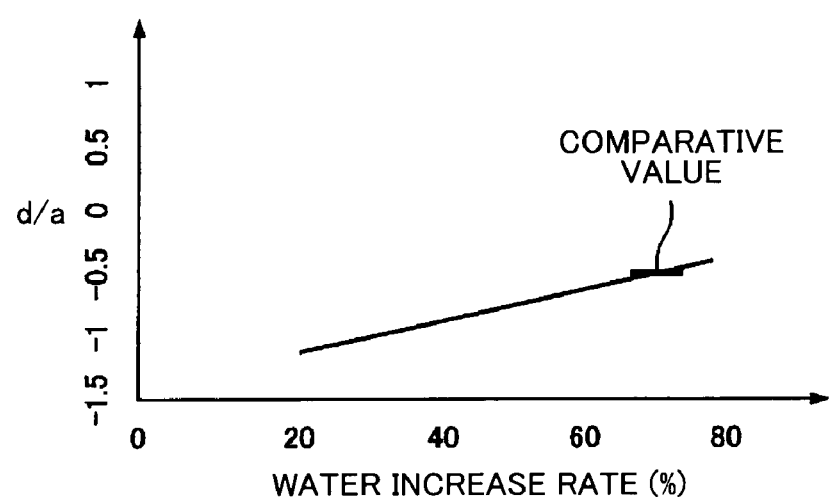
FIG. 12 is a characteristic diagram showing a correlation between an index b/a and a water increase rate.
Figure 13:
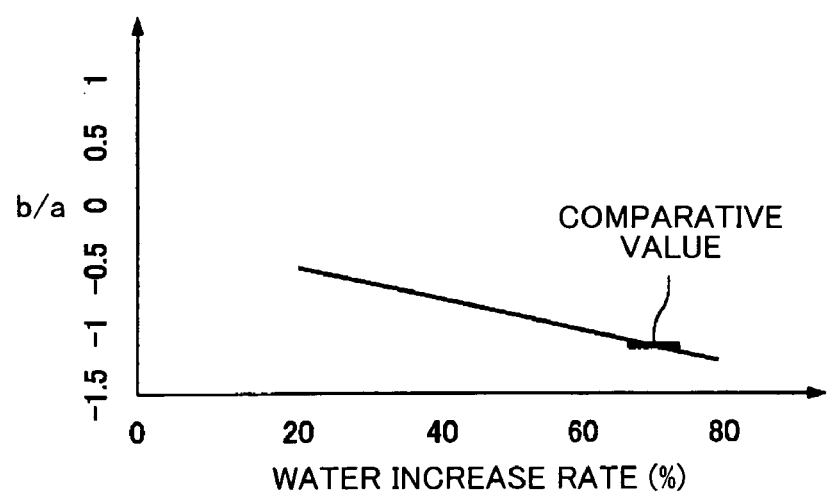
FIG. 13 is a characteristic diagram showing a correlation between an index d/a and a water increase rate.

Since the chronic dialysis patient cannot remove wastes and water by himself after hemodialysis, the blood water content is increased after hemodialysis. Therefore, the blood water content is gradually increased after hemodialysis contrary to the water removal during hemodialysis. Therefore, in the case where the device of the present invention is attached to the chronic dialysis patient in daily life, the index b/a has a negative correlation with the water increase rate, and the index d/a has a positive correlation with the water increase rate differing from FIG. 11. FIGS. 12 and 13 show relations between the index b/a and the index d/a and the water increase rate estimated based on FIG. 11.

The hemodialysis timing determination section 90 shown in FIG. 5 determines that hemodialysis becomes necessary when the index b/a or the index d/a reaches the comparative value (blood water content upper limit or water increase upper limit) shown in FIG. 12 or 13. The comparative value is the index b/a or the index d/a corresponding to the water increase rate (70%, for example) at the time when hemodialysis is necessary. The notification section 100 shown in FIG. 5 notifies the patient (subject) of the hemodialysis time based on output of the hemodialysis timing determination section 90. The hemodialysis timing determination section 90 and the notification section 100 shown in FIG. 3 notify the patient or doctor of the time when hemodialysis is necessary or completed in the same manner as in FIG. 5, although the index differs from the index in FIG. 5.

The period of time from the pulse height "a" shown in FIG. 7 corresponding to the pulse height P0 shown in FIG. 4 to the pulse height "e" shown in FIG. 7 corresponding to the dicrotic notch P3 shown in FIG. 4 may be handled as the ejection time ED. The period of time from the pulse height "e" to the next pulse height "a" may be handled as the diastolic time DT (ED+DT=one cycle of heartbeat or pulse wave). The ratio of the ejection time to one cycle of the heartbeat or pulse wave (ED/(ED+DT)) is hereinafter called "normalized ejection time". The ratio of the diastolic time to one cycle of the heartbeat or pulse wave (DT/(ED+DT)) is hereinafter called "normalized diastolic time".

As another example of the above index, the ejection time ED from the pulse height "a" to the pulse height "e", the diastolic time from the pulse height "e" to the next pulse height "a", the normalized ejection time, or the normalized diastolic time can be given.

For example, since the volume of blood is decreased as the dialysis progresses, a period of time in which the aortic valve opens is decreased as the dialysis progresses. Therefore, the ejection time ED or the normalized ejection time is decreased and the diastolic time DT or the normalized diastolic time is increased as the dialysis progresses. Since the blood water content is increased during the non-dialysis period contrary to the dialysis period, the ejection time ED or the normalized ejection time is increased and the diastolic time DT or the normalized diastolic time is decreased with time. Therefore, if the ejection time ED or the normalized ejection time is measured based on the pulse height "a" and the pulse height "e" of the second differential waveform, it can be determined that dialysis is completed or necessary when the ejection time ED or the normalized ejection time reaches the comparative value. If the diastolic time DT or the normalized diastolic time is measured, it can be determined that dialysis is completed or necessary when the diastolic time DT or the normalized diastolic time reaches the comparative value.

Figure 14:
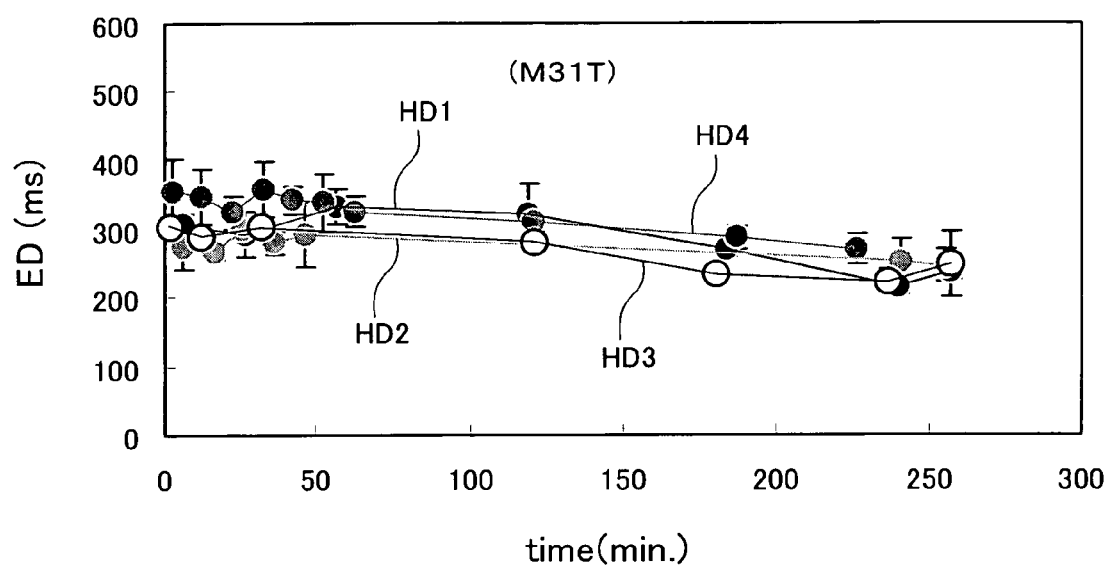
FIG. 14 is a measurement diagram of an index ED measured during four times of dialysis.

FIG. 14 shows measurement results for the ejection time ED during four times (HD1 to HD4) of dialysis of a patient differing from the chronic renal failure patient shown in FIG. 8.

Figure 15:
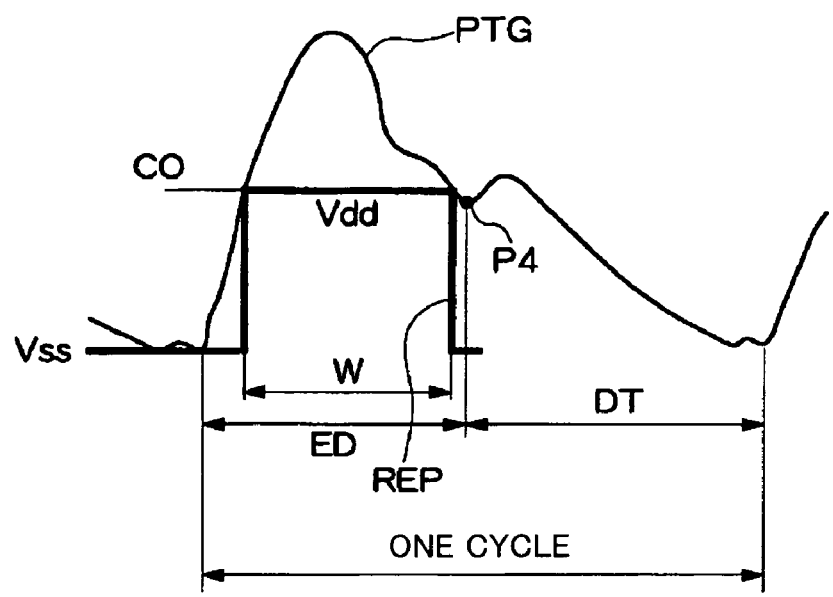
FIG. 15 is a characteristic diagram showing a rectangular wave which is generated by comparing a pulse wave with a comparative value by using a comparator and has a correlation with an ejection time.

The ejection time and the diastolic time are not necessarily calculated from the second differential waveform. As shown in FIG. 15, the index extraction section 80 shown in FIG. 3 may include a comparator in which a comparative value CO is set near the wave height of the dicrotic notch P3 of the pulse wave PTG from which the body movement waveform is eliminated. The output of the comparator is a rectangular wave REP shown in FIG. 15. FIG. 15 shows the rectangular wave REP in the pulse wave PTG for convenience of illustration. A high level of the rectangular wave is at a first power supply potential Vdd of the comparator, and a low level of the rectangular wave is at a second power supply potential Vss.

The pulse width W of the rectangular wave has a correlation with the ejection time ED from the point P0 to the dicrotic notch P3. Therefore, a time interval corresponding to the pulse width W of the rectangular wave is taken as the ejection time ED. The diastolic time DT is calculated by subtracting the ejection time ED from one cycle of the pulse wave or heartbeat calculated by using another method.

Figure 16:
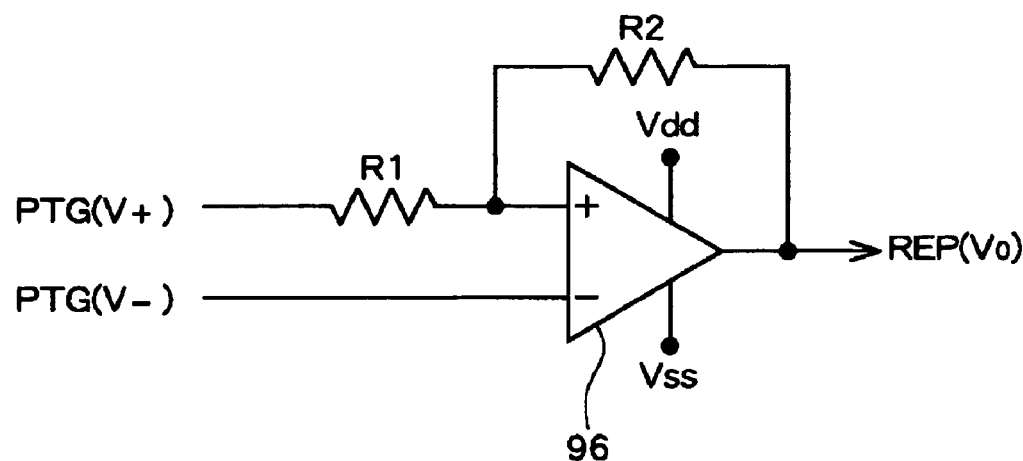
FIG. 16 is a circuit diagram of a comparator with hysteresis which generates the rectangular wave shown in FIG. 15 from a pulse wave.

The comparator is preferably a comparator 96 with hysteresis shown in FIG. 16. The comparator 96 with hysteresis is positively fed back by connecting a feed back resistor R2 with a positive (+) input terminal.

A voltage input to the positive (+) input terminal is expressed by $(V_0-V_+) \times R_1/(R_1+R_2)+V_+$. The output voltage $V_0$ is always saturated at one of the first and second power supply potentials Vdd and Vss which drive the comparator 96.

Therefore, $(V_0-V_+)$ is always greater than 0, and a voltage input to the positive input terminal is always greater than the voltage level $V_+$ of the pulse wave PTG. The number of apparent positive input voltages is increased by the positive feed back effect. Therefore, if the output voltage $V_0$ is saturated at either Vdd or Vss, the output voltage is not easily inverted even if the input is changed. In the case where the output voltage $V_0$ is saturated at Vdd, the output is not immediately inverted even if the voltage $V_+$ of the pulse wave PTG becomes lower than the voltage $V_-$ of the reference value CO. Therefore, since the rectangular wave REP does not easily rise after it has fallen near the dicrotic notch P3 in FIG. 15, the rectangular wave REP can be generated securely.

Low-cut Section

The low-cut section 70 for improving accuracy of detection or determination is described below.

The low-cut section 70 removes a low frequency component due to changes caused by activities of the autonomic nervous system (excluding movement of blood vessels) from the pulse wave detected by the pulse wave detection section 60. Such a low frequency component is not a frequency component of the pulse wave which occurs when the blood flows from the aorta to the peripheral vessels based on expansion and contraction of the heart, and is a frequency component lower than the frequency component in the pulse wave. Since the low frequency component is superimposed on the pulse wave and becomes noise, the pulse wave can be detected stably by eliminating the noise.

The low-cut section 70 may also remove a low frequency component caused by body movement of a subject in a resting state. Even if the subject is in a resting state, the body of the subject is moving (body movement) in order to maintain the resting state. The body movement is comparatively slow differing from the case where the subject rapidly moves the limbs consciously. Therefore, since the low frequency component originating from the body movement is superimposed on the pulse wave and becomes noise, this low frequency component is also removed.

It is preferable that the low-cut section 70 sets the low-cut frequency range from 0.4 to 0.5 Hz in order to remove the low frequency component due to changes caused by activities of the autonomic nervous system (excluding movement of blood vessels) and the low frequency component caused by the body movement. The features of the pulse wave are not included in the low frequency component lower than the above low-cut frequency. Moreover, such a low frequency component becomes noise. As changes caused by activities of the autonomic nervous system, changes caused by activities of the sympathetic nervous system and the parasympathetic nervous system can be given. As the low frequency component due to changes caused by activities of the sympathetic nervous system, a low frequency component due to changes in the muscle pump function which occurs about every 10 seconds (about 0.1 Hz, for example), and the like can be given. As a low frequency component due to changes caused by activities of the parasympathetic nervous system, a low frequency component caused by respiratory activities (about 0.15 Hz, for example), and the like can be given.

The low-cut section 70 may be formed by a band-pass filter in which a high-cut frequency is set in the range of 16 to 30 Hz in addition to the above low-cut frequency. This enables a useless high frequency component exceeding the high-cut frequency to be removed in addition to the low frequency component. It suffices that the high-cut frequency be set at 30 Hz. The high-cut frequency may be set at 20 Hz or 16 Hz.

SPECIFIC CONFIGURATION EXAMPLE 1

Figure 17:
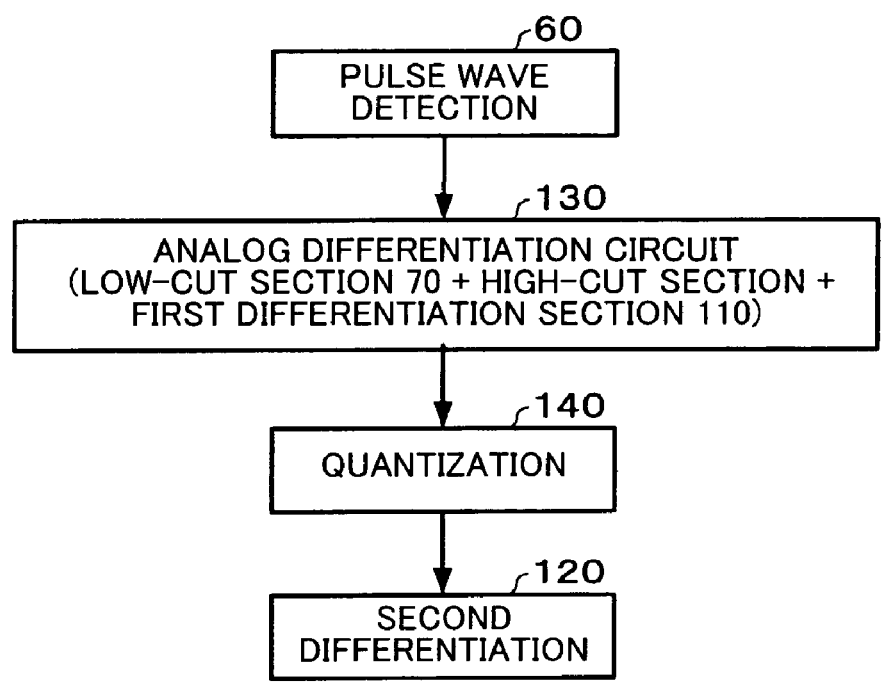
FIG. 17 is a block diagram showing the specific configuration 1 of circuits on stages following the low-cut circuit.
Figure 18:
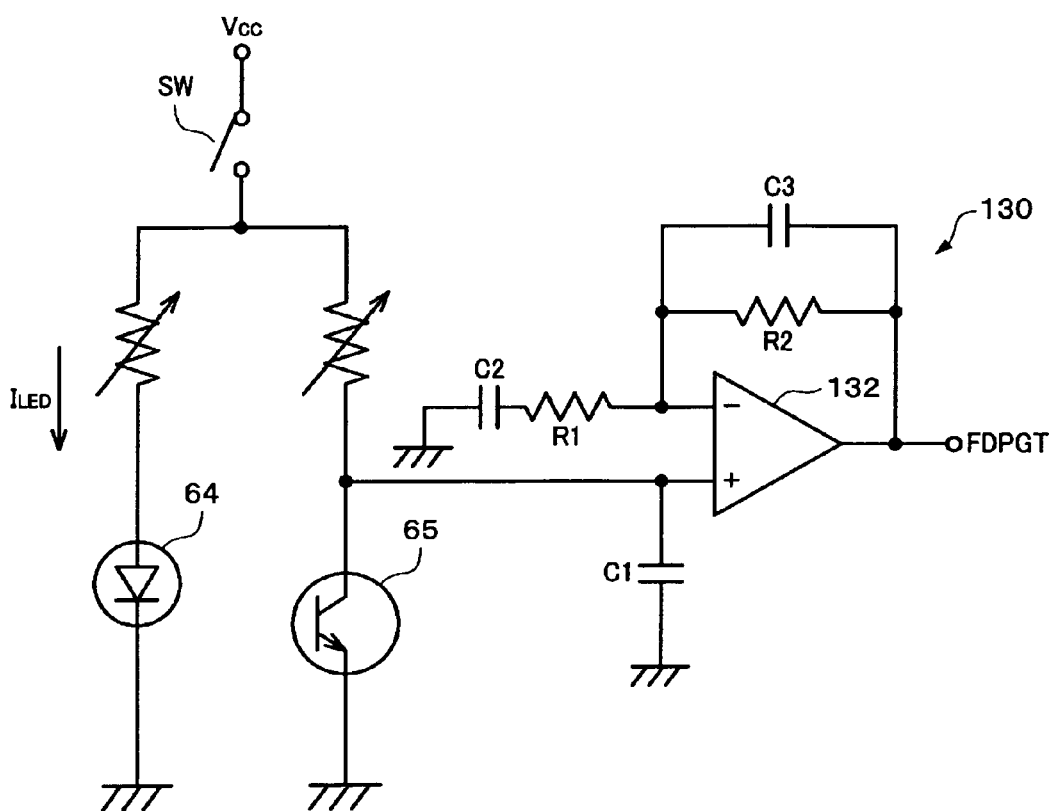
FIG. 18 is a circuit diagram of an analog differentiation circuit shown in FIG. 17.

FIG. 17 is a block diagram showing the pulse wave detection section 60 to the second differentiation section 120 in the functional block shown in FIG. 5 in more detail. FIG. 18 is a circuit diagram of the low-cut section. As shown in FIG. 17, the configuration example 1 includes the pulse wave detection section 60, an analog differentiation circuit 130, a quantization section 140, and the second differentiation section 120. The analog differentiation circuit 130 has a function of a high-cut section in addition to the functions of the low-cut section 70 and the first differentiation section 110 shown in FIG. 5. In other words, the analog differentiation circuit 130 has a bandpass function. The analog differentiation circuit 130 may have a high-pass function instead of the bandpass function. In both cases, a low frequency component lower than a low-cut frequency of 0.4 to 0.5 Hz can be cut.

As shown in FIG. 18, the analog differentiation circuit 130 may have a configuration in which elements C1 to C3 and R1 and R2, each having a predetermined constant, are connected to a positive input terminal, a negative input terminal, and a negative feed-back path of an operational amplifier 132. The analog differentiation circuit 130 is provided with a bandpass function which allows a frequency component in a frequency band of 0.4 to 30 Hz, 0.4 to 20 Hz, or 0.4 to 16 Hz to pass depending on setting of the constants of these elements. The low-cut frequency is set at 0.4 to 0.5 Hz.

The quantization section 140 is an analog-digital converter which quantizes the analog signal output from the analog differentiation circuit 130 to convert the analog signal into a digital signal as shown in FIG. 19A. As the quantization method, various conventional methods may be employed. In the case where the light emitting element 64 is turned on and off by using the switch SW shown in FIGS. 2 and 18, since the output waveform has been sampled by the switching, the signal is sampled at a sampling rate equivalent to the switching cycle. In this case, the quantization section 120 preferably amplifies the input signal so that the amplitude of the output signal is equal to or greater than a predetermined level within the dynamic range by using an automatic gain control (AGC) function. The vascular bed under the skin of the subject is present in the light transmission path between the light emitting element 64 and the light receiving element 65 of the pulse wave detection section 60. Therefore, the output signal of the pulse wave detection section 60 must be appropriately amplified within the dynamic range.

The second differentiation section 120 shown in FIG. 17 is a quantization differentiation section which obtains the amount of change (or inclination) of two different points on the time base shown in FIG. 19. In more detail, as shown in FIG. 20, the second differentiation section 120 may be formed by first and second storage sections 124 and 126 in which data is alternately stored by using a switch 122, and a digital subtracter 128 which calculates the difference between the data output from the first and second storage sections 124 and 126. FIG. 19 is a waveform chart showing a quantization waveform and a differential waveform of the quantization waveform. A second differential waveform shown as (B) in the chart is the amount of change of the data shown as (A) in the chart.

EXPERIMENTAL EXAMPLE

The original waveform PTG, the first differential waveform FDPTG, and the second differential waveform SDPTG of three subjects A to C were collected while changing the bandpass characteristics of the analog differentiation circuit 130. As the bandpass band, the high-cut frequency was 16 Hz, and the low-cut frequency was 0.1 Hz (Comparative Example 1), 0.2 Hz (Comparative Example 2), 0.43 Hz (Example 1), and 0.6 Hz (Comparative Example 3).

Figure 23A:
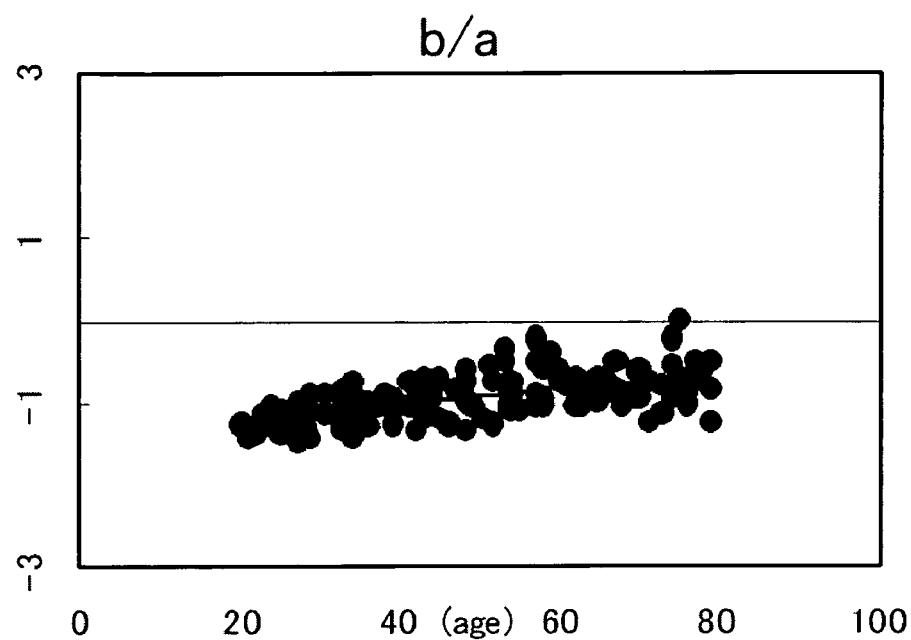
FIG. 23A is a characteristic diagram showing the correlation between an index (b/a) and the age of subjects.
Figure 23B:
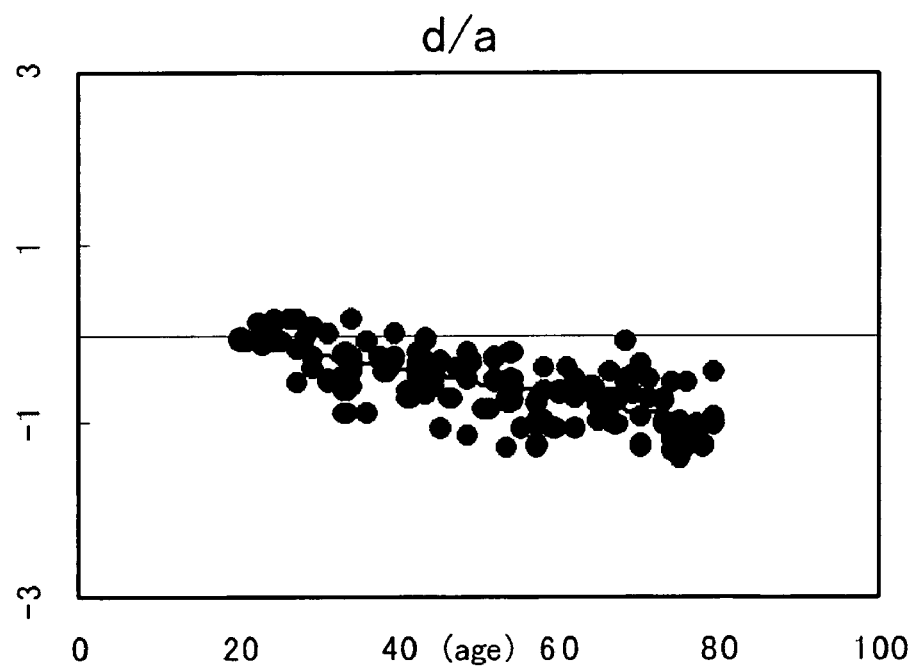
FIG. 23B is a characteristic diagram showing the correlation between an index (d/a) and the age of subjects.

The index b/a was calculated from each second differential waveform SDPTG detected in this manner. The index b/a changes depending on the blood water content of each subject, and has a negative correlation with the age of the subject as shown in FIG. 23A (−b/a has a positive correlation). From the results for the above measurement, it was confirmed that the index −b/a (=1.12) of the second differential waveform SDPTG in Example 1 (low-cut frequency=0.43 Hz) for a subject A is an optimum value for the age of the subject A. FIG. 23B shows that the index d/a has a positive correlation with the age of the subject.

The measurements were also carried out for a subject B who is older than the subject A and a subject C who is younger than the subject A. The index −b/a of the subject B measured in Example 1 was 1.18, and the index −b/a of the subject C measured in Example 1 was 0.89. The correlation that "age of subject C<age of subject A<age of subject B" coincides with the correlation that "index of subject C (0.89)<index of subject A (1.12)<index of subject B (1.18)" in the order of age. Therefore, it was confirmed that the low-cut frequency in Example 1 (0.43 Hz) is optimum as the low-cut frequency of the bandpass characteristics as compared to Comparative Examples 1 to 3. As described above, 0.4 to 0.5 Hz is optimum as the low-cut frequency, and it is not preferable that the low-cut frequency be lower (0.1 Hz and 0.2 Hz) or higher (0.6 Hz) than 0.4 to 0.5 Hz as in Comparative Examples 1 to 3.

SPECIFIC CONFIGURATION EXAMPLE 2

Figure 21:
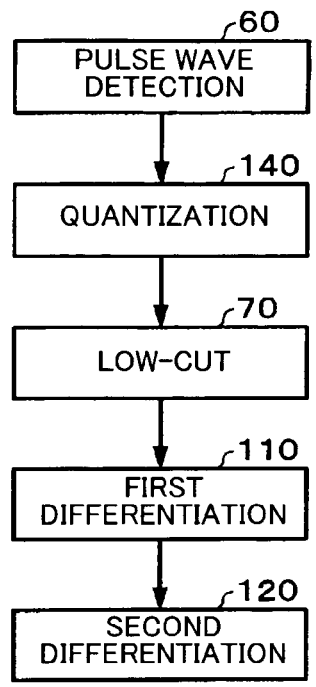
FIG. 21 is a block diagram showing the specific configuration 2 of circuits on stages following the low-cut circuit.

FIG. 21 shows a modification example in which the quantization section 140 is provided between the pulse wave detection section 60 and the low-cut section 70. The function of the quantization section 140 is the same as that shown in FIG. 17. The functions of the first and second differentiation sections 110 and 120 are the same as those shown in FIG. 17. One of the first and second differentiation sections 110 and 120 may be an analog differentiation circuit.

Figure 22:
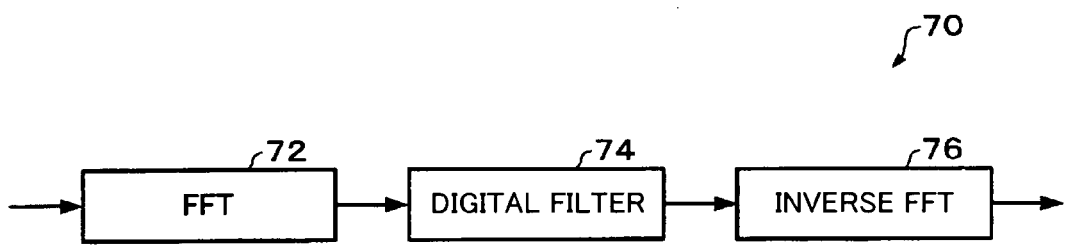
FIG. 22 is a circuit diagram of a low-cut section shown in FIG. 21.

As shown in FIG. 22, the low-cut section 70 shown in FIG. 21 includes a Fourier transformation section 72 which performs Fourier transformation of the quantized data, a digital filter 74 which removes a frequency spectrum lower than the low-cut frequency, and an inverse Fourier transformation section 76 which performs inverse Fourier transformation of the output of the digital filter. A low frequency component can be removed by removing the frequency spectrum lower than the low-cut frequency among the frequency spectra obtained by Fourier transformation.

The low-cut section 70 may process the analog signal. The quantization section 140 may be provided between the low-cut section 70 and the first differentiation circuit 110, and the first and second differentiation sections 110 and 120 may be formed as digital differentiation circuits.

The present invention is not limited to the above-described embodiments. Various modifications and variations are possible within the spirit and scope of the present invention.

What is claimed is:

1. A blood water content detection device comprising:
   a pulse wave detection section which noninvasively detects a peripheral pulse wave; and
   an index extraction section which extracts an index which changes depending on a blood water content from the detected pulse wave.

2. The blood water content detection device as defined in claim 1,
   wherein the index extraction section extracts the index based on a pulse height of a dicrotic notch in the pulse wave.

3. The blood water content detection device as defined in claim 2,
   wherein the index extraction section extracts as the index a first ratio of a pulse height of a first rise point of one cycle of the pulse wave and a pulse height of the dicrotic notch.

4. The blood water content detection device as defined in claim 3,
wherein the index extraction section further extracts a reference index which is less dependent on the blood water content than the first ratio, and outputs a ratio of the index to the reference index.

5. The blood water content detection device as defined in claim 4,
wherein the index extraction section extracts as the reference index a second ratio of the pulse height of the first rise point of one cycle of the pulse wave and a pulse height of a dicrotic wave.

6. The blood water content detection device as defined in claim 1,
wherein the index extraction section extracts the index based on a pulse height of an ejection wave in the pulse wave.

7. The blood water content detection device as defined in claim 6,
wherein the index extraction section extracts a first ratio of a pulse height of a first rise point of one cycle of the pulse wave and a pulse height of the ejection wave.

8. The blood water content detection device as defined in claim 7,
wherein the index extraction section further extracts a reference index which is less dependent on the blood water content than the first ratio, and outputs a ratio of the index to the reference index.

9. The blood water content detection device as defined in claim 8,
wherein the index extraction section extracts as the reference index a second ratio of the pulse height of the first rise point of one cycle of the pulse wave and a pulse height of a dicrotic wave.

10. The blood water content detection device as defined in claim 1, further comprising:
a low-cut section which removes a low frequency component due to changes caused by activities of an autonomic nervous system from the pulse wave detected by the pulse wave detection section.

11. The blood water content detection device as defined in claim 10,
wherein the low-cut section further removes a low frequency component caused by body movement of a subject in a resting state.

12. The blood water content detection device as defined in claim 10,
wherein the low-cut section sets the low-cut frequency range from 0.4 to 0.5 Hz.

13. The blood water content detection device as defined in claim 10,
wherein the low-cut section is formed of a bandpass filter which sets the high-cut frequency range from 16 to 30 Hz.

14. The blood water content detection device as defined in claim 1, further comprising:
a first differentiation section which differentiates the pulse wave; and
a second differentiation section which differentiates the pulse wave differentiated by the first differentiation section, wherein:
a second differential waveform which is output from the second differentiation section has five inflection points having pulse heights "a" to "e" sequentially output on a time base within one cycle; and
the index extraction section extracts the index based on at least one of the five pulse heights.

15. The blood water content detection device as defined in claim 14,
wherein the index extraction section extracts a pulse height ratio (d/a).

16. The blood water content detection device as defined in claim 14,
wherein the index extraction section extracts a pulse height ratio (b/a).

17. The blood water content detection device as defined in claim 14,
wherein the index extraction section extracts a pulse height ratio [(d/a)/(b/a)].

18. The blood water content detection device as defined in claim 14,
wherein the index extraction section extracts a pulse height ratio [(d/a)/(e/a)].

19. The blood water content detection device as defined in claim 14,
wherein the index extraction section extracts a pulse height ratio [(b/a)/(e/a)].

20. The blood water content detection device as defined in claim 1,
wherein the index extraction section extracts as the index a cardiac ejection time from the pulse wave.

21. The blood water content detection device as defined in claim 1,
wherein the index extraction section extracts as the index a cardiac diastolic time from the pulse wave.

22. The blood water content detection device as defined in claim 1,
wherein the index extraction section extracts as the index a ratio of a cardiac ejection time to one cycle of the pulse wave from the pulse wave.

23. The blood water content detection device as defined in claim 1,
wherein the index extraction section extracts as the index a ratio of a cardiac diastolic time to one cycle of the pulse wave from the pulse wave.

24. A hemodialysis timing determination device comprising:
the blood water content detection device as defined in claim 1; and
a determination section which determines the timing of hemodialysis based on the output of the blood water content detection device.

25. The hemodialysis timing determination device as defined in claim 24,
wherein the determination section compares the index output from the blood water content detection device with a comparative value corresponding to a blood water content upper limit, and determines the time when hemodialysis is necessary based on the comparison result.

26. The hemodialysis timing determination device as defined in claim 24,
wherein the determination section compares the index output from the blood water content detection device with a comparative value corresponding to a blood water content lower limit, and determines the time when hemodialysis is completed based on the comparison result.

* * * * *